United States Patent [19]

Rutter

[11] Patent Number: 4,769,326

[45] Date of Patent: Sep. 6, 1988

[54] EXPRESSION LINKERS

[75] Inventor: William J. Rutter, San Francisco, Calif.

[73] Assignee: The Regents of the University of California, Calif.

[21] Appl. No.: 599,464

[22] Filed: Apr. 12, 1984

Related U.S. Application Data

[63] Continuation of Ser. No. 403,405, Jul. 20, 1982, abandoned, which is a continuation of Ser. No. 125,878, Feb. 29, 1980, abandoned.

[51] Int. Cl.$^4$ ..................... C12P 21/00; C12N 15/00; C07H 21/04
[52] U.S. Cl. ..................... 435/68; 435/320; 435/172.3; 536/27
[58] Field of Search ............ 536/27, 28, 29; 435/172.3, 317

[56] References Cited

U.S. PATENT DOCUMENTS

4,321,365  3/1982  Wu et al. .................. 536/27

FOREIGN PATENT DOCUMENTS

001929  5/1979  European Pat. Off. .

OTHER PUBLICATIONS

Bahl et al., Gene, vol. 1, pp. 81-92, 1976.
Goeddel et al., Proc. Natl. Acad. Sci., vol. 76, pp. 106-110, 1979.
Scheller et al., Science, vol. 196, pp. 177-180, 1977.
Martial, Science, vol. 205, pp. 602-606, 1979.
Chang et al., Nature, vol. 275, pp. 617-624, 1978.
Marians et al., Nature, vol. 263, pp. 744-748, 1976.
Heyneker et al., Nature, vol. 263, pp. 748-752, 1976.
Stryer, Lubert; *Biochemistry*, 1981, W. H. Freeman and Company, New York, pp. 25 & 26 (photocopied).

*Primary Examiner*—Blondel Hazel
*Attorney, Agent, or Firm*—Lisabeth Feix Murphy

[57] ABSTRACT

The present invention is based upon a general principle of providing specific oligonucleotide segments ("linkers", herein) to be attached in sequence to a cloned DNA coding segment. The linkers of the present invention confer desired functional properties on the expression of the protein coded by the coding sequence. Using linkers of the present invention, the desired protein may be expressed either as a fusion or non-fusion protein. A linker coding for an additional sequence of amino acids may be attached, the sequence being chosen to provide properties exploitable in a simplified purification process. A linker coding for an amino acid sequence of the extended specific cleavage site of a proteolytic enzyme is provided, as well as specific cleavage linkers for simpler specific cleavage sites.

7 Claims, No Drawings

EXPRESSION LINKERS

This is a continuation of application Ser. No. 403,405, filed July 20, 1982, abandoned, which is a continuation of application Ser. No. 125,878, filed Feb. 29, 1980, now abandoned.

BACKGROUND OF THE INVENTION

The invention herein provides for deoxynucleotide sequences coding for amino acid sequences which contain specific cleavage sites. The deoxynucleotide sequences are herein termed specific cleavage linkers and are useful in recombinant DNA technology.

Recent advances in biochemistry and in recombinant DNA technology have made it possible to achieve the synthesis of specific proteins under controlled conditions independent of the higher organism from which they are normally isolated. Such biochemical synthetic methods employ enzymes and subcellular components of the protein synthesizing machinery of living cells, either in vitro, in cell-free systems, or in vivo, in microorganisms. In either case, the key element is provision of a deoxyribonucleic acid (DNA) of specific sequence which contains the information necessary to specify the desired amino acid sequence. Such a specific DNA is herein termed a DNA coding segment. The coding relationship whereby a deoxynucleotide sequence is used to specify the amino acid sequence of a protein is described briefly, infra, and operates according to a fundamental set of principles that obtain throughout the whole of the known realm of living organisms.

A cloned DNA may be used to specify the amino acid sequence of proteins synthesized by in vitro systems. DNA-directed protein synthesizing systems are well-known in the art, see, e.g., Zubay, G., *Ann. Rev. Genetics* 7, 267 (1973). In addition, single-stranded DNA can be induced to act as messenger RNA in vitro, resulting in high fidelity translation of the DNA sequence (Salas, J. et al, *J. Biol. Chem.* 243, 1012 (1968). Other techniques well known in the art may be used in combination with the above procedures to enhance yields.

Developments in recombinant DNA technology have made it possible to isolate specific genes or portions thereof from higher organisms, such as man and other mammals, and to transfer the genes or fragments to a microorganism, such as bacteria or yeast. The transferred gene is replicated and propagated as the transformed microorganism replicates. As a result, the transformed microorganism may become endowed with the capacity to make whatever protein the gene or fragment encodes, whether it be an enzyme, a hormone, an antigen or an antibody, or a portion thereof. The microorganism passes on this capability to its progeny, so that in effect, the transfer has resulted in a new strain, having the described capability. See, for example, Ullrich, A. et al., *Science* 196, 1313 (1977), and Seeburg, P. H., et al., *Nature* 270, 486 (1977). A basic fact underlying the application of this technology for practical purposes is that DNA of all living organisms, from microbes to man, is chemically similar, being composed of the same four nucleotides. The significant differences lie in the sequences of these nucleotides in the polymeric DNA molecule. The nucleotide sequences are used to specify the amino acid sequences of proteins that comprise the organism. Although most of the proteins of different organisms differ from each other, the coding relationship between nucleotide sequence and amino acid sequence is fundamentally the same for all organisms. For example, the same nucleotide sequence which is the coding segment for the amino acid sequence of human growth hormone in human pituitary cells, will, when transferred to a microorganism, be recognized as coding for the same amino acid sequence.

Abbreviations used herein are given in Table 1.

TABLE 1

| | |
|---|---|
| DNA — deoxyribonucleic acid | A — Adenine |
| RNA — ribonucleic acid | T — Thymine |
| cDNA — complementary DNA (enzymatically synthesized from an mRNA sequence) | G — Guanine |
| | C — Cytosine |
| | U — Uracil |
| mRNA — messenger RNA | ATP — adenosine triphosphate |
| dATP — deoxyadenosine triphosphate | TTP — Thymidine triphosphate |
| dGTP — deoxyguanosine triphosphate | EDTA — Ethylenediaminetetraacetic acid |
| dCTP — deoxycytidine triphosphate | |

The coding relationships between nucleotide sequence in DNA and amino acid sequence in protein are collectively known as the genetic code, shown in Table 2.

TABLE 2

Genetic Code

| | | | |
|---|---|---|---|
| Phenylalanine(Phe) | TTK | Histidine(His) | CAK |
| Leucine(Leu) | XTY | Glutamine(Gln) | CAJ |
| Isoleucine(Ile) | ATM | Asparagine(Asn) | AAK |
| Methionine(Met) | ATG | Lysine(Lys) | AAJ |
| Valine(Val) | GTL | Aspartic acid(Asp) | GAK |
| Serine(Ser) | QRS | Glutamic acid(Glu) | GAJ |
| Proline(Pro) | CCL | Cysteine(Cys) | TGK |
| Threonine(Thr) | ACL | Tryptophan(Try) | TGG |
| Alanine(Ala) | GCL | Arginine(Arg) | WGZ |
| Tyrosine(Tyr) | TAK | Glycine(Gly) | GGL |
| Termination signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

| | |
|---|---|
| A = adenine | J = A or G |
| G = guanine | K = T or C |
| C = cytosine | L = A, T, C or G |
| T = thymine | M = A, C or T |
| X = T or C if Y is A or G | |
| X = C if Y is C or T | |
| Y = A, G, C or T if X is C | |
| Y = A or G if X is T | |
| W = C or A if Z is A or G | |
| W = C if Z is C or T | |
| Z = A, G, C or T if W is C | |
| Z = A or G if W is A | |
| QR = TC if S is A, G, C or T | |
| QR = AG if S is T or C | |
| S = A, G, C or T if QR is TC | |
| S = T or C if QR is AG | |

An important feature of the code, for present purposes, is the fact that each amino acid is specified by a trinucleotide sequence, also known as a nucleotide triplet. The phosphodiester bonds joining adjacent triplets are chemically indistinguishable from all other internucleotide bonds in DNA. Therefore the nucleotide sequence cannot be read to code for a unique amino acid sequence without additional information to determine the reading frame, which is the term used to denote the grouping of triplets used by the cell in decoding the genetic message.

In procaryotic cells, the endogenous coding segments are typically preceded by nucleotide sequences having the functions of initiator of transcription (mRNA synthesis) and initiator of translation (protein synthesis), termed the promoter and ribosomal binding site, respectively. The coding segment begins around 3–11 nucleotides distant from the ribosomal binding site. The exact number of nucleotides intervening between the ribosomal binding site and the initiation codon of the coding segment does not appear to be critical for translation of the coding segment in correct reading frame. The term "expression control segment" is used herein to denote the nucleotide sequences comprising a promoter, ribosomal binding site and a 3–11 nucleotide spacer following the ribosomal binding site. In Eukaryotic cells, regulation of transcription and translation may be somewhat more complicated, but also involve such nucleotide sequences.

Many recombinant DNA techniques employ two classes of compounds, transfer vectors and restriction enzymes, to be discussed in turn. A transfer vector is a DNA molecule which contains, inter alia, genetic information which insures its own replication when transferred to a host microorganism strain. Examples of transfer vectors commonly used in bacterial genetics are plasmids and the DNA of certain bacteriophages. Although plasmids have been used as the transfer vectors for the work described herein, it will be understood that other types of transfer vectors may be employed. Plasmid is the term applied to any autonomously replicating DNA unit which might be found in a microbial cell, other than the genome of the host cell itself. A plasmid is not genetically linked to the chromosome of the host cell. Plasmid DNA's exist as double-stranded ring structures generally on the order of a few million daltons molecular weight, although some are greater than $10^8$ daltons in molecular weight. They usually represent only a small percent of the total DNA of the cell. Transfer vector DNA is usually separable from host cell DNA by virtue of the great difference in size between them. Transfer vectors carry genetic information enabling them to replicate within the host cell, in most cases independently of the rate of host cell division. Some plasmids have the property that their replication rate can be controlled by the investigator by variations in the growth conditions. By appropriate techniques, the plasmid DNA ring may be opened, a fragment of heterologous DNA inserted, and the ring reclosed, forming an enlarged molecule comprising the inserted DNA segment. Bacteriophage DNA may carry a segment of heterologous DNA inseted in place of certain non-essential phage genes. Either way, the transfer vector serves as a carrier or vector for an inserted fragment of heterologous DNA.

Transfer is accomplished by a process known as transformation. During transformation, host cells mixed with plasmid DNA incorporate entire plasmid molecules into the cells. Although the mechanics of the process remain obscure, it is possible to maximize the proportion of host cells capable of taking up plasmid DNA and hence of being transformed, by certain empirically determined treatments. Once a cell has incorporated a plasmid, the latter is replicated within the cell and the plasmid replicas are distributed to the daughter cells when the cell divides. Any genetic information contained in the nucleotide sequence of the plasmid DNA can, in principle, be expressed in the host cell. Typically, a transformed host cell is recognized by its acquisition of traits carried on the plasmid, such as resistance to certain antibiotics. Different plasmids are recognizable by the different capabilities or combination of capabilities which they confer upon the host cell containing them. Any given plasmid may be made in quantitiy by growing a pure culture of cells containing the plasmid and isolating the plasmid DNA therefrom.

Restriction endonucleases are hydrolytic enzymes capable of catalyzing site-specific cleavage of DNA molecules. The locus of restriction endonuclease action is determined by the existence of a specific nucleotide sequence. Such a sequence is termed the recognition site for the restriction endonuclease. Restriction endonucleases from a variety of sources have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive, and may be used to rejoin the hydrolyzed DNA. Since any DNA susceptible of cleavage by such an enzyme must contain the same recognition site, the same cohesive ends will be produced, so that it is possible to join heterologous sequences of DNA which have been treated with a restriction endonuclease to other sequences similarly treated. See Roberts, R. J., *Crit. Rev. Biochem.* 4, 123 (1976). Restriction sites are relatively rare, however the general utility of restriction endonucleases has been greatly amplified by the chemical synthesis of double stranded oligonucleotides bearing the restriction site sequence. Therefore virtually any segment of DNA can be coupled to any other segment simply by attaching the appropriate restriction oligonucleotide to the ends of the molecule, and subjecting the product to the hydrolytic action of the appropriate restriction endonuclease, thereby producing the requisite cohesive ends. See Heynecker, H. L., et al., *Nature* 263, 748 (1976) and Scheller, R. H., et al., *Science* 196, 177 (1977). An important feature of the distribution of restriction endonuclease recognition sites is the fact that they are randomly distributed with respect to reading frame. Consequently, cleavage by restriction endonuclease may occur between adjacent codons or it may occur within a codon.

More general methods of DNA cleavage or for end sequence modification are available. A variety of non-specific endonucleases may be used to cleave DNA randomly, as discussed infra. End sequences may be modified by creation of oligonucleotide tails of dA on one end and dT at the other, or of dG and dC, to create sites for joining without the need for specific linker sequences.

The term "expression" is used in recognition of the fact that an organism seldom if ever makes use of all its genetically endowed capabilities at any given time. Even in relatively simple organisms such as bacteria, many proteins which the cell is capable of synthesizing are not synthesized, although they may be synthesized under appropriate environmental conditions. When the protein product, coded by a given gene, is synthesized by the organism, the gene is said to be expressed. If the protein product is not made, the gene is not expressed. Normally, the expression of genes in *E. coli* is regulated as described generally, infra, in such manner that proteins whose function is not useful in a given environment are not synthesized and metabolic energy is conserved.

The means by which gene expression is controlled in *E. coli* and yeast is well understood, as the result of extensive studies over the past twenty years. See, generally, Hayes, W., *The Genetics of Bacteria And Their Viruses,* 2d edition, John Wiley & Sons, Inc., New York (1968), and Watson, J. D., *The Molecular Biology of the Gene,* 3d edition, Benjamin, Menlo Park, Calif. (1976). These studies have revealed that several genes, usually those coding for proteins carrying out related functions in the cell, may be found clustered together in continuous sequence. The cluster is called an operon. All genes in the operon are transcribed in the same direction, beginning with the codons coding for the N-terminal amino acid of the first protein in the sequence and continuing through to the C-terminal end of the last protein in the operon. At the beginning of the operon, proximal to the N-terminal amino acid codon, there exists a region of the DNA, termed the control region, which includes a variety of controlling elements including the operator, promoter and sequences for the binding of ribosomes. The function of these sites is to permit the expression of those genes under their control to be responsive to the needs of the organism. For example, those genes coding for enzymes required exclusively for utilization of lactose are normally not appreciably expressed unless lactose or an analog thereof is actually present in the medium. The control region functions that must be present for expression to occur are the initiation of transcription and the initiation of translation. The minimal requirements for independent expression of a coding segment are therefore a promoter, a ribosomal binding site, and a 3-11 nucleotide spacer segment. The nucleotide sequences contributing these functions are relatively short, such that the major portion of an expression control segment might be on the order of 15 to 25 nucleotides in length. Expression of the first gene in the sequence is initiated by the initiation of transcription and translation at the position coding for the N-terminal amino acid of the first protein of the operon. The expression of each gene downstream from that point is also initiated in turn, at least until a termination signal or another operon is encountered with its own control region, keyed to respond to a different set of environmental cues. While there are many variations in detail on this general scheme, the important fact is that to be expressed in a host such as *E. coli.* or a eukaryotic such as yeast a gene must be properly located with respect to a control region having initiator of transcription and initiator of translation functions.

It has been demonstrated that genes not normally part of a given operon can be inserted within the operon and controlled by it. The classic demonstration was made by Jacob, F., et al., *J. Mol. Biol.* 13, 704 (1965). In that experiment, genes coding for enzymes involved in a purine biosynthesis pathway were transferred to a region controlled by the lactose operon. The expression of the purine biosynthetic enzyme was then observed to be repressed in the absence of lactose or a lactose analog, and was rendered unresponsive to the environmental cues normally regulating its expression.

In addition to the operator region regulating the initiation of transcription of genes downstream from it, there are known to exist codons which function as stop signals, indicating the C-terminal end of a given protein. See Table 2. Such codons are known as termination signals and also as nonsense condons, since they do not normally code for any amino acid. Deletion of a termination signal between structural genes of an operon creates a fused gene which could result in the synthesis of a chimeric or fusion protein consisting of two amino acid sequences coded by adjacent genes, joined by a peptide bond. That such chimeric proteins are synthesized when genes are fused was demonstrated by Benzer, S., and Champe, S. P., *Proc. Nat. Acad. Sci USA* 48, 114 (1962).

Once a given gene has been isolated, purified and inserted in a transfer vector, the over-all result of which is termed the cloning of the gene, its availability in substantial quantity is assured. The cloned gene is transferred to a suitable microorganism, wherein the gene replicates as the microorganism proliferates and from which the gene may be reisolated by conventional means. Thus is provided a continuously renewable source of the gene for further manipulations, modifications and transfers to other vectors or other loci within the same vector.

Expression has been obtained in the prior art by transferring the cloned gene, in proper orientation and reading frame, into a control region such that read-through from the host gene results in synthesis of a chimeric protein comprising the amino acid sequence coded by the cloned gene. Techniques for constructing an expression transfer vector having the cloned gene in proper juxtaposition with a control region are described in Polisky, B., et al., *Proc. Nat. Acad. Sci USA* 73, 3900 (1976); Itakura, K., et al., *Science* 198, 1056 (1977); Villa-Komaroff, L., et al., *Proc. Nat. Acad. Sci USA* 75, 3727 (1978); Mercereau-Puijalon, O., et al., *Nature* 275, 505 (1978); Chang, A. C. Y., et al., *Nature* 275, 617 (1978), and in copending U.S. application Ser. No. 933,035 by Rutter, et al., filed Aug. 11, 1978, said application incorporated herein by reference as though set forth in full.

As described in Ser. No. 933,035, the cloned gene is joined to a host control fragment in order to obtain expression of the gene. This control fragment may consist of no more than that part of the control region providing for initiation of transcription and initiation of translation, or may additionally include a portion of a structural gene, depending on the location of the insertion site. Thus, the expression product would be either a protein coded by the cloned gene, hereinafter referred to as a non-fusion protein, or a fusion protein coded in part by the procaryotic structural gene, in part by the cloned gene, and in part by any intervening nucleotide sequences linking the two genes. The peptide bond between the desired protein or peptide, comprising the C-terminal portion of the fusion protein, and the remainder, is herein termed the "junction bond".

After the protein has been produced, it must then be purified. Several advantages and disadvantages exist for the purification of either the non-fusion protein or the fusion protein. The non-fusion protein is produced within the cell. As a consequence, the cells must be lysed or otherwise treated in order to release the non-fusion protein. The lysate will contain all of the proteins of the cell in addition to the non-fusion protein, which may make purification of the protein difficult. Another consequence is that the non-fusion protein may be recognized as a foreign protein and undergo rapid degradation within the cell. Therefore non-fusion proteins may not be obtainable in reasonable yields. A major advantage of a non-fusion protein is that the protein itself is the desired final product.

The stability of the expression product is frequently enhanced by expression of a fusion protein. The host portion of the fusion protein frequently stabilizes the expression product against intracellular degradation. Further, it is often possible to choose a host protein which is protected from degradation by compartmentalization or by excretion from the cell into the growth medium. The cloned gene can then be attached to the host gene for such a protein. A fusion protein consisting of an excreted or compartmentalized host protein (N-terminal) and an eucaryotic protein (C-terminal), is likely to be similarly excreted from the cell or compartmentalized within it because the signal sequence of amino acids that confers secretability is on the N-terminal portion of the fusion protein. In the case pf a fusion protein excreted into the cell medium, purification is greatly simplified. In some instances, the host portion may have distinctive physical properties that permit the use of simple purification procedures. A major disadvantage of the fusion protein is that the host protein must be removed from the fusion protein in order for the eucaryotic protein to be obtained.

Direct expression as a non-fusion protein will generally be preferred if the protein is stable in the host cell. In many instances, the disadvantage of having to purify the expression product from a cell lysate will be overcome by the advantage of not having to employ specific cleavage means to remove an N-terminal portion. Most advantageously, as provided herein by the present invention, the desired protein may be expressed as a fusion protein comprising an N-terminal sequence having distinctive physical properties useful for purification and provided with a structure at the junction point with the desired C-terminal portion such that the junction bond, as defined supra, can be cleaved by means which do not appreciably affect the desired C-terminal protein or peptide.

Many methods for chemical cleavage of peptides have been proposed and tested. Spande, T. F., et al, *Adv. Protein Chem.* 24, 97 (1970). However, many of these are non-specific, i.e. they cleave at many sites in a protein. See also a brief discussion in *The Proteins*, 3rd Ed., Neurath, H. and Hill, R. L., Ed., Academic Press, Vol. 3, pp. 50-57 (1977). Hydrolysis of peptide bonds is catalyzed by a variety of known proteolytic enzymes. See *The Enzymes*, 3rd Ed., Boyer, P. D., Ed., Academic Press, Vol. III (1971); *Methods in Enzymology*, Vol. XIX, Perlmann, G. E. and Lorand, L. Ed., Academic Press (1970); and, *Methods in Enzymology*, Vol. XLV, Lorand L., Ed., Academic Press (1976). However, many proteolytic enzymes are also non-specific, with respect to the cleavage site.

The specificity of each chemical or enzymatic means for cleavage is generally described in terms of amino acid residues at or near the hydrolyzed peptide bond. The hydrolysis of a peptide bond in a protein or polypeptide is herein termed a cleavage of the protein or polypeptide at the site of the hydrolyzed bond. The peptide bonds which are hydrolyzed by chemical or enzymatic means are generally known. (See the above-identified references.) For example, trypsin (3.4.4.4) cleaves on the carboxyl side of an arginine or lysine residue. (The number in parentheses after the enzyme is its specific identifying nomenclature as established by the International Union of Biochemists.) Thus, trypsin is said to be specific for arginine or lysine. Since trypsin hydrolyzes only on the carboxyl side of arginine or lysine residues, it is said to have a narrow specificity. Pepsin (3.4.4.1), on the other hand, has a broad specificity and will cleave on the carboxyl side of most amino acids but preferably phenylalanine, tyrosine, tryptophan, cysteine, cystine or leucine residues. A few specific chemical cleavage reactions are known. For example, CNBr will cleave only at methionine residues under appropriate conditions. However, the difficulty with all specific cleavage means, whether chemical or enzymatic, which depend upon the existence of a single amino acid residue at or near the cleavage point is that such methods will only be useful in specific instances where it is known that no such residue occurs internally in the amino acid sequence of the desired protein. The larger the desired protein, the greater the likelihood that the sensitive residue will occur internally. Therefore, a technique generally useful for cleaving fusion proteins at a desired point is preferably based upon the existence of a sequence of amino acids at the junction bond which has a low likelihood of occurrence internally in the desired protein.

The specificity for the site of the hydrolyzed peptide bond is generally termed the primary specificity of the enzyme. Thus, trypsin has a primary specificity for arginine and lysine residues. The primary specificity of enzymes has been the subject of considerable investigation. It has determined that a particular enzyme would recognize and bind the amino acid residue within a protein molecule corresponding to the enzyme's primary specificity and cleave the protein at that point. The part of an enzyme which recognizes and binds the substrate and catalyzes the reaction is known as the active site. For example, trypsin would recognize and bind an arginine residue within a protein and cleave the protein on the carboxyl side of the arginine. For many years it was thought that only the amino acid residues corresponding to the primary specificity affected the specificity of hydrolysis of the peptide bond by the enzyme. However, it has been noted that amino acids in the immediate vicinity of the site of hydrolysis may affect the binding affinity of the enzyme at that site. Several examples of this effect can be shown for trypsin. Considering the sequence —x—Arg—y where x and y are amino acids, it has been found that the binding affinity of trypsin at the Arg—y bond is significantly reduced when x is Glu or Asp. Similarly, it has been shown that the binding affinity at an arginine or lysine residue, in repetitive sequences of lysine, arginine or combination thereof, is greater than if a single arginine or lysine residue were present. That is, the enzyme preferentially binds at —Arg—Arg—X compared to y—Arg—x. Also, trypsin does not appear to hydrolyze the —Arg—Pro— or —Lys—Pro peptide bind. See Kasper, C. B., at p. 137 in *Protein Sequence Determination*, Needleman, S. B., Ed. Springer-Verlag, New York (1970).

Recently, it has also been determined that amino acids in the vicinity of the site of hydrolysis will also be recognized and bound by the enzyme. For example, Schechter, I. et al., *Biochem. Biophys. Res. Comm.*, 27, 157 (1967) reported that papain (3.3.4.10) binds several amino acid residues in its active site as determined from the hydrolysis of peptides of various lengths. An active site which binds several amino acids is often termed an extended active site. The specificity of an enzyme for the additional amino acids not at the immediate site of hydrolysis is sometimes termed the secondary specificity of the enzyme. It has now been shown that many enzymes have extended active sites. Several additional examples of enzymes having extended active sites include: elastase (3.4.4.7)—Thompson, R.C., et al., *Proc. Nat. Acad. Sci. USA* 67, 1734 (1970); α-chymotrypsin (3.4.4.5)—Bauer, C. A., et al., *Biochem.* 15, 1291 and 1296 (1976); chymosin (3.4.23.4)—Visser, S., et al., *Biochem. Biophys. Acta* 438 265 (1976); and enterokinase (3.4.4.8)—Maroux, S., et al., *J. Biol. Chem.* 246, 5031 (1971). (See also Fruton, J. S., *Cold Spring Harbor Conf. Cell Prolif.* 2, 33 (1975).) The extended active site appears to at least increase the catalytic efficiency of the enzyme. It may also increase the binding affinity of the enzyme for the peptide. See Fruton, J. S., supra. For example, Schechter, I. et al., *Biochem. Biophys. Res. Comm.* 32, 898 (1969) found that the phenylalanine in the sequence —x—Phe—y—z where x, y and z are amino acids enhances the susceptibility of the peptide to hydrolysis by papain and directs the enzymatic attack at the y—z peptide bond. Valine and leucine may also provide similar results when substituted for Phe in the above sequence. This could be an explanation for the broad specificity of papain. See Glazer, A. N. et al at p. 501 in *The Enzymes,* supra. Thus, an enzyme may have a narrow specificity as a result of its primary specificity alone or in combination with its secondary specificity (i.e., the enzyme has an extended active site).

The present invention provides for the prokaryotic or eucaryotic expression of a cloned coding segment such that the desired protein is produced, either as a fusion protein or a non-fusion protein, as desired, and may be provided with specific additional amino acid sequences to permit specific cleavage at the junction bond of a fusion protein and to permit rapid purification. The general invention provides a number of options for the investigator, depending on the size and function of the desired protein, and upon the relative advantages of expression as a fusion or non-fusion protein, according to principles well known in the art, as discussed supra.

To provide generally useful means for specific cleavage of the junction bond, a chemical or enzymatic cleavage means having a narrow specificity will not be suitable except in special cases. A cleavage means is not suitable if its cleavage site occurs within the eucaryotic protein of the fusion protein. For example, a eucaryotic protein may contain several arginine and/or lysine residues. Trypsin would cleave on the carboxyl side of these residues. Since cleavage would occur within the eucaryotic protein, trypsin would not be suitable for use for the present invention. This is also true for many chemical cleavage means. Thus, it can be seen that in order to obtain more specific cleavage, it may be necessary to utilize a cleavage means which will have a cleavage site in a specific amino acid sequence having two or more amino acid residues. For example, it would be desirable for the cleavage means to be specific for an amino acid sequence —x—y—z— and to cleave on the carboxyl side of the z residue. The probability of a similar sequence occurring within the eucaryotic protein would be very small. Therefore, the probability of cleavage within the eucaryotic protein would also be very small. The entire eucaryotic protein can then be removed and purified.

The present invention is designed such that, when a fusion protein is expressed, a specific cleavage sequence of one or more amino acids is inserted between the host portion and the eucaryotic portion of the fusion protein. If the sequence of the eucaryotic portion is known, it is possible to select a specific cleavage sequence of only one amino acid residue so long as that residue does not appear in the eucaryotic protein. It is preferred, however, to utilize a specific cleavage sequence which contains two or more amino acid residues sometimes referred to herein as an extended specific cleavage sequence. This type of sequence takes advantage of the extended active sites of various enzymes. By utilizing an extended specific cleavage sequence, it is highly probable that cleavage will only occur at the desired site, the junction bond, and not within the desired protein. The present invention is important in recombinant DNA technology. By inserting a specifically recognized amino acid sequence between the host protein portion and the desired portion of a fusion protein, it is now possible to specifically cleave the desired portion out of the fusion protein without further affecting the desired portion.

For practical purposes, as contemplated by the present invention, the specificity of cleavage at the junction need not be all or nothing with respect to other potential cleavage sites in the desired protein. It suffices if the junction bond cleavage site is sufficiently favored kinetically, either due to increased binding affinity or enhanced turnover time, that the junction bond is cleaved preferentially with respect to other sites, such that a reasonable yield of the desired protein can be obtained. Reaction conditions of temperature, buffer, ratio of enzyme to substrate, reaction time and the like can be selected so as to maximize the yield of the desired protein, as a matter of ordinary skill in the art.

One enzyme which may cleave at a specific cleavage site has been called a signal peptidase. For several eucaryotic and procaryotic proteins, the initial translation product is not the protein itself, but the protein with approximately 20 additional amino acids on the amino terminus of the protein. The additional amino acid sequence is called a signal peptide. The signal peptide is thought to be a specific signal for the vectorial transport of the synthesized protein into the endoplasmic reticulum and is cleaved away from the protein during this phase. See Blobel, G. et al, *J. Cell Biol.* 67, 835 (1975). A specific cleavage enzyme, i.e., signal peptidase, has been observed in a cell-free system which hydrolyzes the peptide bond between the signal peptide and the active protein in association with passage through a cell membrane. See Blobel, G. et al, *Proc. Nat. Acad. Sci. USA* 75, 361 (1978).

The present invention provides for the synthesis of a specific cleavage linker which can be attached to the end of the isolated DNA segment coding for the N-terminus of the protein prior to insertion of the segment into the transfer vector. The specific cleavage linker codes for an amino acid sequence which contains a specific cleavage site which does not occur within the desired protein. Thus, the specific cleavage within the linker amino acid sequence results in the isolation of the desired protein from the fusion protein. An advantage of the present invention is the cleavage at the amino-terminal side of the first amino acid of the N-terminus of the desired protein. Another advantage is that little of the desired protein is degraded during the cleavage procedure.

For the purpose of providing expression as a non-fusion protein, the present invention provides synthetic oligonucleotide linkers comprising a promoter, a ribosomal binding site, and a 3–11 nucleotide spacer. This linker, coupled with a coding segment, provides for direct expression of the coding segment when inserted into a transfer vector and used to transform a suitable host. Using such a linker, the coding segment may be expressed even though inserted in a "silent" region of the vector, thus increasing the range of choice of suitable insertion sites. Preferably, direct expression of the coding segment is obtained without resortin to a synthetic promoter segment. A ribosomal binding site linker, together with a 3-11 nucleotide spacer, directs the reinitiation of translation of mRNA initiated at a naturally occurring promoter site. Therefore, as long as the coding segment and expression linker are inserted in a transfer vector gene under natually occurring promoter control, reinitiation at the inserted ribosomal binding site results in direct expression of the attached coding segment. Most preferably, the insertion is made adjacent to the existing promoter, between it and the structural gene it normally controls.

For the purpose of improving purification of the fusion or non-fusion protein, the present invention provides a linker coding for amino acid sequences which function to enhance ease of purification. For example, a polyanionic amino acid segment or a polycationic or hydrophobic segment will be tightly bound by a variety of known solid phase adsorbents or column materials. Specific amino acid sequences recognizable by specific binding substances can be incorporated on either end of the desired protein to render it purifiable by affinity chromatography. Such purification segments can be used in conjunction with a specific cleavage segment to provide for simple quantitative purification of fusion or non-fusion proteins followed by specific cleavage of the purification segment and quantitative removal thereof.

The foregoing purposes are achieved in the present invention according to the properties of each system, to solve the individual problems presented in preparing the desired protein. The principles of the present invention as discussed herein provide generally applicable means for expressing a coding segment as a fusion protein, or a non-fusion protein, with or without a purification segment, specifically cleavable from any protein or peptide not part of the desired expression product.

SUMMARY OF THE INVENTION

The present invention is based upon a general principle of providing specific oligonucleotide segments ("linkers", herein) to be attached in sequence to a cloned DNA coding segment. The linkers of the present invention confer desired functional properties on the expression of the protein coded by the coding sequence. Using linkers of the present invention, the desired protein may be expressed either as a fusion or non-fusion protein. A linker coding for an additional sequence of amino acids may be attached, the sequence being chosen to provide properties exploitable in a simplified purification process. A linker coding for an amino acid sequence of the extended specific cleavage site of a proteolytic enzyme is provided, as well as specific cleavage linkers for simpler specific cleavage sites.

The oligonucleotide linkers used are termed "segments" herein. Thus, the oligonucleotide coding for a specific cleavage site is termed a specific cleavage segment; that coding for initiation of transcription and translation is termed an expression control segment; that coding for reinitiation translation is termed an expression segment; and that coding for specific purification is termed a purification segment. The cloned nucleotide sequence coding for the desired protein is termed the coding segment. The expression product is a protein or polypeptide bearing various identifiable portions; where the desired protein or peptide is expressed as a fusion protein, the N-terminal amino acid sequence contributed by the host or transfer vector genome is termed the host portion; where a specific cleavage linker has been employed, the amino acid sequence resulting from its expression is termed the specific cleavage portion; and where a purification segment has been attached, its expression product is termed the purification portion. That portion coded by the cloned coding segment is termed the desired protein, which term will be used herein to denote any size of polypeptide, polyamino acid, protein or protein fragment specified by the coding segment.

It is contemplated that the linkers of the present invention may be attached to either end of the coding segment, to provide the desired portion at either the amino end or the carboxyl end of the desired protein. It will be understood that for the expression of any portion attached to the carboxyl end of the desired protein, the coding segment must not contain a termination codon. It will further be understood that linkers designed for the expression of a portion attached to the carboxyl end of the desired protein must include a termination codon, appropriately located at the end of the segment whose expression is desired.

The present invention opens a variety of options for the expression of a cloned coding segment, depending on the properties of the desired protein and of the host expressing it. The host may be either prokaryotic or eukaryotic. Where the desired protein is small or unstable in the host, it may be preferred to express a fusion protein. The use of a specific cleavage linker of the present invention will then enable the subsequent specific removal of the host portion of the fusion protein. It may be further desired to include a purification segment thereby providing a region of the fusion protein conferring functional properties exploitable to provide simplified purification prior to specific cleavage. Following specific cleavage, the purification portion remains attached to the host portion and simplifies the separation of the host portion from the desired protein. In some instances, it may be preferable to express the desired protein as a non-fusion protein. In that case, the use of an expression segment or an expression control segment linker conveniently provides for direct expression of the coding segment. It will be understood that such direct expression depends upon the existence of an initiation codon. If the initiation codon is not included in the coding segment, it can be provided as part of the expression segment. Where an N-terminal methionine is not desired, a specific cleavage segment may be interposed between the initiating methionine codon and the coding segment. A purification segment linker may be included to provide for rapid purification of the expression product. Alternatively, the use of an expression segment linker may be followed by a linker coding for a signal peptide which can cause the secretion of the expression product from the host cell.

The particular combination of linkers chosen to aid in the expression of a given desired protein will depend upon the nature of the desired protein and upon functional properties of the expression system. Some of the described linkers are appropriate for prokaryotic and eukaryotic hosts, while others are specific for a particular type of host cell. Such choices will be made as a matter of ordinary skill. Other combinations of the described linkers not specifically disclosed herein are contemplated as within the scope of the present invention.

DETAILED DESCRIPTION OF THE INVENTION

The specific cleavage linkers are deoxynucleotide sequences coding for amino acid sequences which contain specific cleavage sites. A specific cleavage linker is attached to a coding segment prior to its transfer to a microorganism. The advantage of a specific cleavage linker is that it provides a specific cleavage sequence having a specific cleavage site at the junction bond of the fusion protein. This bond can be cleaved to produce the desired protein.

Using current recombinant DNA technology, it is possible to insert an isolated coding segment into a transfer vector, transform a microorganism with this transfer vector, and under appropriate conditions have the coding segment expressed by the microorganism. Frequently, it is desirable to connect the coding segment to a portion of a host gene, which codes for a protein that is normally excreted from the cell. This is done so that the expression product, a fusion protein comprising a host protein portion and the desired protein, is compartmentalized or excreted from the cell into the culture medium. This process is desirable because it reduces or eliminates the degradation of the desired protein within the cell. In the case of a fusion protein excreted into the culture medium, it is easier to purify the fusion protein. The fusion protein is easier to purify because there is less total protein in the culture medium than in a whole cell lysate.

A separate advantage of fusion protein expression is that there are frequently well-known means for purifying the host portion. Such means will often be applicable to the fusion protein as well. Affinity chromatography is especially preferred, where applicable.

The major difficulty encountered with this process is the need to remove the desired protein from the host portion in the fusion protein. This step is required in order to purify the desired protein. This is difficult because there is usually not a specific cleavage site located between the amino terminus of the desired portion and the carboxy terminus of the host portion which can be attacked uniquely by specific chemical or enzymatic means. Thus, the present invention provides for the incorporation of a specific cleavage sequence between the desired protein and the host portion of the fusion protein.

There are many methods for cleaving proteins as discussed above. Examples of chemical means include cyanogen bromide (CNBr) and hydroxylamine. See Spande, T. F. et al., supra. Examples of proteolytic enzymes include trypsin, papain, pepsin, thrombin (3.4.4.13) and enterokinase. See *The Proteins*, supra, *Meth. Enzymol.*, Vol. XIX, supra, and *Meth. Enzymol.*, Vol. XLV, supra. However, many of these means do not show enough specificity to be useful for the present invention. That is, many of these means only recognize a specific amino acid residue and cleave at this point. Thus, except in very few situations, these same means will cause cleavage to occur within the desired protein.

The present invention undertakes to create a situation for protein similar to restriction endonucleases for DNA. As discussed above, a restriction enzyme will recognize a specific sequence of DNA and cleave the DNA at this point. The present invention provides for a specific amino acid sequence containing one or more amino acid residues which is recognized by a particular chemical or enzymatic cleavage means. The specific amino acid sequence is incorporated into a fusion protein between the host portion and the desired protein. This is accomplished by chemically synthesizing a deoxynucleotide sequence which codes for the specific amino acid sequence. This DNA sequence is then attached to an isolated gene prior to its incorporation in a transfer vector. This DNA sequence is herein termed a specific cleavage linker. The specific amino acid sequence is herein termed a specific cleavage portion. The specific cleavage portion contains a specific cleavage site. The specific cleavage portion is selected so that it does not or is unlikely to occur within the desired protein. In this manner, the desired protein is separated from the host portion of the fusion protein without itself being degraded.

In selecting a specific cleavage sequence, several factors must be considered. If the amino acid sequence of the desired protein is known, it is a fairly simple matter to select a specific cleavage sequence. In this case it is preferred that the specific cleavage sequence not be found within the desired protein. For example, human proinsulin does not contain any methionines. Therefore, methionine could be selected as the specific cleavage sequence. If the DNA sequence coding for methionine (ATG) were attached to the isolated human proinsulin gene prior to insertion in a transfer vector, the fusion protein produced upon expression could be treated with CNBr under appropriate conditions to cleave human proinsulin from the host protein. See Konigsberg, W. H. et al. at p. 2 in *The Proteins*, supra. Similarly, human proinsulin does not containg the sequence X-Phe-Arg-Y. The enzyme kalikrein B (3.4.21.8) recognizes this sequence and cleaves on the carboxyl side of the arginine. See Fiedler, F. at p. 289 in *Meth. Enzymol.*, Vol. XLV, supra. Thus, by attaching the DNA sequence coding for Phe-Arg (TTK WGZ) to the isolated human proinsulin gene prior to insertion, the fusion protein produced upon expression could be cleaved with kallikrein B to obtain human proinsulin. Thus, when the desired protein sequence is known, it is possible to select any amino acid sequence as the specific cleavage sequence which is specifically recognized by a chemical or enzymatic cleavage means and does not appear in the desired protein sequence.

Selecting the specific cleavage sequence is more difficult where the amino acid sequence of the desired protein is unknown. In this case, it is preferred to use a sequence having at least two amino acid residues. The greater the number of amino acid residues in the specific cleavage sequence, the more unlikely the probability of a similar sequence occurring within the desired protein. This would increase the probability of uniquely cleaving the desired protein from the host portion. When at least two amino acid residues are required for the specific recognition site, the preferred cleavage means is enzymatic. One possible chemical means which could be used is hydroxylamine. Hydroxyalamine cleaves the -Asn-Z-bond where Z may be Gly, Leu or Ala. The rate of hydrolysis of Z=Gly is much faster than for Z=Leu or Ala. See Konigsberg, W. H. et al, supra.

Another factor which can effect the selection of the specific cleavage sequence is the rate of hydrolysis of a particular cleavage means for similar amino acid sequences. For example, enzyme A recognizes and cleaves on the carboxyl side of C or D in the following amino acid sequences: -A-B-C- or -A-B-D-. However, the rate of hydrolysis of the former is much greater than that for the latter. Assume -A-B-C- is chosen as the specific recognition sequence and -A-B-D- exists in the protein. By exhaustive hydrolysis with enzyme A it is possible to get cleavage on the carboxyl side "C" and on the carboxyl side of "D". However, the rate of hydrolysis for A-B-C- is much greater than that for -A-B-D- so that most of the initial cleavages will occur in A-B-C-, i.e., on the carboxyl side of C. Therefore, a selective cleavate at the desired site can be achieved by resorting to a partial hydrolysis. Although the yield may be reduced, it should still be significant enough to warrant the use of enzyme A in this situation. However, this situation is not the preferred one.

The extended active site is the most important factor to consider in selecting the appropriate enzyme. The enzyme must be able to recognize at least two amino acid residues and preferably more than two. This will decrease the probability of cleavage within the desired protein as discussed above. For example, an enzyme which recognizes the amino acid sequence -X-Y-Z- and cleaves on the carboxyl side Z would be useful for the present invention. An enzyme which recognizes a sequence of several amino acids but may cleave on the carboxyl side of two different amino acids when substituted in the sequence may also be useful if the rates of hydrolysis for the two are different as discussed above. An enzyme which cleaves in the inner part of the specific cleavage sequence would also be useful when used in conjunction with specific aminopeptidases. For example, an enzyme which recognizes the amino acid sequence -A-B-C-D- and cleaves on the carboxyl side of B would be useful when used in conjunction with an aminopeptidase which would specifically cleave C-D from the remainder of the desired protein. This enzyme would also be useful if C-D- is the N-terminus of the desired protein.

It is contemplated that any enzyme which recognizes a specific sequence and causes a specific cleavage can be utilized for the present invention. This specific recognition and cleavage may be the function of the enzyme under its normal enzymatic conditions or under special restricted conditions. For example, it has been shown that Aspergillopeptidase B has a very narrow specificity at 0° C., whereas it has a fairly broad specificity at 37° C. See Spadari, S. et al., *Biochim. Biophys. Acta* 359, 267 (1974). The following enzymes are examples of enzymes which are expected to be useful for the present invention: enterokinase, kallikrein B or chymosin. Enterokinase recognizes the sequence X-(Asp)$_n$-Lys-Y where n=2-4 and cleaves on the carboxyl side of Lys. The rate of binding increases by 10-20 times as n increases from 2 to 4, as shown by studies with synthetic peptides. See Maroux, S. et al., supra. It has recently been determined that Glu or a combination of Asp and Glu can be substituted for the Asp and that Arg can be substituted for Lys. See Liepnieks, J., Ph. D. Thesis, Purdue University (1978). Kallikrein B recognizes the sequence X-Phe-Arg-Y are cleaves on the carboxyl side of Arg. See Fiedler, F. supra. Chymosin recognizes the sequence X-Pro-His-Leu-Ser-Phe-Met-Ala-Ile-Y and cleaves the Phe-Met bond. See Vesser, S. et al., supra, and Vesser, S. et al., *Biochem. Biophys. Acta* 481, 171 (1977). Two other enzymes which should prove to be useful once their extended active sites have been studied thoroughly are urokinase (3.4.99.26) and thrombin. Urokinase has been shown to recognize and cleave only an Arg-Val bond found in the sequence X-Arg-Val-Y of plasminogen. See Robbins, K. C., et al., *J. Biol. Chem.* 242, 2333 (1967). Thrombin cleaves on the carboxyl side of Arg but will only cleave at specific arginyl bonds. It has been shown that the sequence X-Phe-(Z)$_6$-Arg-Y where Z can be any combination of amino acids is present in several of the substrates for thrombin. See Magnusson, S. at p. 277 in *The Enzymes*, Vol. III, supra.

Another enzyme which may be useful is the "signal peptidase." See Blobel, G., supra, and Jackson, R. C. et al., *Proc. Nat. Acad. Sci. USA* 74, 5598 (1977). This enzyme recognizes and cleaves the signal peptide from a protein. By incorporating the signal peptide between the desired protein and the host portion of the fusion protein, specific cleavage may be accomplished during secretion of the fusion protein from the host to yield the desired protein.

Any chemical or enzymatic means which recognizes a specific sequence and causes a specific cleavage can be utilized for the present invention. First, the appropriate cleavage means for a particular desired protein is chosen. Then a DNA sequence is chemically synthesized which codes for the specific amino acid cleavage sequence dictated by the appropriate cleavage means. The DNA sequence is synthesized by the phosphotriester method as described by Itakura, K. et al, *J. Biol. Chem.* 250, 4592 (1975), and Itakura, K. et al, *J. Am. Chem. Soc.* 97, 7326 (1975) or other suitable synthetic means. For example, where enterokinase is the cleavage means, a DNA sequence which codes for Asp-Asp-Asp-Asp-Lys—as an example—is synthesized. This DNA sequence would then be GAK$_1$GAK$_2$GAK$_3$-GAK$_4$AAJ$_5$. A preferred DNA sequence will be based upon a consideration of the codons preferentially employed in the host cell. For example, in *E. coli*, the preferred DNA sequence would be GATGATGAT-GATAAA. DNA coding for a desired protein is isolated using conventional techniques, such as the cDNA technique. See, for example, Ullrich, A. et al, supra, and Seeburg, P. H. et al, supra. The chemically synthesized DNA sequence is then attached to the isolated DNA by DNA ligase- catalyzed blunt end ligation as described by Sgaramella, V. et al, *Proc. Nat. Acad. Sci, USA* 67, 1468 (1970). This specific cleavage linker-gene DNA is then treated by addition of a second deoxynucleotide sequence containing a restriction site and attaching this second sequence to the specific cleavage linker-gene DNA by DNA ligase-catalyzed blunt end ligation. Restriction site linkers and their use have been described by Heyneker, H. L., et al, supra, and by Scheller, R. L. et al, supra. Such restriction site linkers are modified according to the present invention to provide 0, 1 or 2 additional deoxynucleotides. The latter deoxynucleotides provide for all three reading frames. Alternatively, linkers could be synthesized which contain a restriction linker, 0, 1 or 2 additional deoxynucleotides and a specific cleavage linker. This composite linker could then be attached to the isolated coding sequence by a single blunt end ligation step. Or, two DNA sequences could be synthesized—one containing a restriction linker and 0, 1 or 2 deoxynucleotides and the other containing the specific cleavage linker. These two sequences could be joined by blunt end ligation and then attached to the isolated coding sequence by blunt end ligation. The final product, i.e., restriction linker-0, 1 or 2 deoxynucleotides—specific cleavage linker—DNA coding sequence is then inserted in a transfer vector using conventional techniques. It will be understood in the art that the foregoing steps of blunt end ligation will attach the linker sequences at both ends of the coding segment. However, as the latter will contain or will be provided with a termination codon, the coding sequences attached downstream, in the direction of translation from the termination codon, will remain untranslated. A microorganism can then be transformed with the transfer vector and expression of the gene is obtained under appropriate conditions. Techniques for accomplishing the above are more fully described in copending application of Bell et al, Ser. No. 75,192 filed Sept. 12, 1979 and copending application of Rutter et al, Ser. No. 933,035, filed Aug. 11, 1978, both incorporated herein by reference. The fusion product resulting from expression is purified, preferably as described infra, and subjected to cleavage by the selected means.

Purification segments coding for amino acid sequences that contribute ease of purification can be included as linkers such that the added purification portion is on the N-terminal side of the junction bond and thereby removed following specific cleavage. Such linkers may be separately ligated or incorporated with other linker segments in a single composite linker.

The kinds of amino acid sequences that contribute ease of purification include polyanionic segments (Asp/Glu)$_{5-20}$ and polycationic segments (Lys/Arg-)$_{5-20}$ that will bind readily to ion exchangers. A polyanionic segment can serve a dual function as an enterokinase extended site sequence if provided with a C-terminal lysine or arginine residue. A hydrophobic segment may be (leu/ileu/vol/phe)$_{10-20}$. More specific, single step purification, can be achieved by the use of affinity chromatography. In principle, the affinity adsorbent could bind any part of the expressed protein. Preferably, the specific binding is directed toward that portion destined to be removed from the desired protein. Given a fusion protein, the specific affinity could be an immunochemical binding of the procaryotic portion. Alternatively, the specificity could be provided by the purification segment. For example, a linker segment coding for bradykinin would be incorporated to provide the bradykinin sequence as part of the fusion protein. An immunoadsorbent specific for bradykinin (comprising bradykinin antibody) then specifically binds the fusion protein. The desired protein is then removed from the adsorbed complex by specific cleavage, the unwanted portion remains adsorbed and is readily separated. Other examples will be apparent to those ordinarily skilled in the art. Providing a highly hydrophobic purification segment also permits rapid and specific separation, by absorption to hydrophobic (reverse phase) solid phase carriers, by precipitation, and by differential solubility in non-aqueous media.

A special case of purification linker involves incorporating the signal peptide sequence in the expression product. The amino acid sequences of known signal peptides are sufficiently short to make feasible the synthesis of linkers coding therefor. Since the signal peptide is functional as an N-terminal peptide, its use will be in conjunction with direct expression of the desired protein as a non-fusion protein, as described infra. Furthermore, the use of a specific cleavage linker will be unnecessary, since signal peptides are normally removed from the desired protein product by a signal peptidase endogenous in the host cell. Therefore, the use of a signal peptide linker can result in secretion of the desire protein and removal of the signal peptide, mediated by endogenous host functions.

The appropriate use of linkers according to the present invention provides means for expressing a coding segment as a non-fusion protein. The required linker for such direct expression is an expression control segment comprising a promoter sequence, a ribosomal binding site sequence, and a spacer of about 3-11 nucleotides. Any coding segment providing an initiation codon (ATG) within a distance of 3-11 nucleotides from the ribosomal binding site sequence will be expressed in correct reading frame. It is not necessary to provide a coding segment having ATG as its 5' end, provided the ATG sequence is located within 3-11 nucleotides distance from the ribosomal binding site of the linker. An example of a prokaryotic ribosomal binding site would have the following sequence in its pulse strand: L(n)TAGGAGGAGCC, where L is A, T, C or G, and n may be 0, 1 or 2.[1] The foregoing sequence includes the following elements: a ribosomal binding site sequence substantially homologous with the 3'-end of the 16S ribosomal RNA, as shown by Shine and Dalgarno, *Proc. Nat. Acad. Sci. USA,* 71 1342 (1974), and by Steitz and Jakes, *Proc. Nat. Acad. Sci. USA* 72 4734 (1975). The ribosomal binding sites so far studied are variable in their degree of homology with the 16S ribosomal RNA sequence. The maximum number of complementary bases so far found is seven. The above described sequence contains six. The above-described sequence also contains a stop codon (TAG) which is designed to prevent read-through translation of any message initiated elsewhere. In order that the stop codon be in phase with the message to be terminated, the sequence is provided with 0, 1 or 2 additional nucleotides. The inclusion of a termination codon may not be necessary in some instances. A universal terminator providing termination in all three phases is provided by the sequence TAGLTAGLTAG. The above-described ribosomal binding site segment also contains a BamHI linker sequence, GGATCC. The linker is useful for attaching additional sequence material to the ribosomal binding site segment, for identifying DNA sequences into which the linker has been introduced, and in some instances, for inserting the ribosomal binding site linker.

[1]For convenience, DNA sequences are designated by the plus strand. However, it will be understood that all such linker segments also have a minus strand of complementary base sequence and opposite polarity.

For joining the ribosomal binding site segment to the coding segment, a spacer sequence of 3-11 base pairs is desired. This can be done most conveniently by blunt end ligation of one of the commercially available restriction site linkers (Scheller et al, supra). These linkers can be modified as desired by treatment with the appropriate restriction endonuclease followed by filling or trimming the unpaired ends thus produced to provide the desired spacer sequence. For example, the EcoRI linker GGAATTCC can be treated with endonuclease EcoRI followed by DNA polymerase to fill in the unpaired end to provide the sequence AATTCC. The ribosomal binding site sequence bearing a BamHI linker sequence is similarly treated with BamHI endonuclease and DNA polymerase such that its structure is now L(n)TAGGAGGATC. Blunt end ligation provides the sequence L(n)TAGGAGGATCAATTCC. If a coding segment having a terminal ATG initiation codon is attached, the initiation codon will be eight base pairs from the ribosomal binding site. A second stop codon (TAA) is provided, to prevent read-through translation of earlier initiated messages. Use of the above described technique obviates the need for building in a stop codon earlier in the linker sequence.

The function of a ribosomal binding site linker will vary depending upon the chosen insertion site in the transfer vector. If the insertion interrupts a normally translated message, the ribosomal binding site linker is likely to serve as a reinitiation point for transcription. However, the efficiency of translation may be improved by making the insertion at a site adjacent to an existing, known, promoter, in the direction of normal transcription. For example, insertion at a site adjacent to the promoter of the tryptophan operon will result in direct translation of the inserted segment in place of the normally expressed proteins of the tryptophan operon, under control of the tryptophan promoter If it is desired to insert the coding segment in a silent region of the transfer vector, it will be necessary to provide a promoter sequence to insure proper initiation of transcription.

Sequences which can function as initiators, of prokaryotic transcription are known. See for example Pribnow, D., Proc. Nat. Acad. Sci. USA 72 784 (1975). For example, the sequence TATJATJ, where J is A or G, appears to provide promoter function. In eukaroytes, the sequence TATAA, or similar sequences TATAAT or TATAAG, are found in the region to transcription initiation and are likely to be a part of all promoter regions. See Gaunon, F. et al, Nature 278, 428-34 (1979). However, other nucleotides outside the described sequence can modify its efficiency of promoter function in ways which are not presently predictable. Therefore, while it is presently feasible to provide an expression control segment linker comprising both a synthetic promoter and synthetic ribosomal binding site segments, it is preferred to employ naturally occurring promoters, either separately cloned or by insertion adjacent thereto.

A ribosomal binding site linker suitable for expression in eucaryotic cells is provided by a segment homologous to the terminal sequence of the 18S ribosomal RNA found in eucaryotes, Hagenbuchle, et al, *Cell* 13, 551 (1978). The sequence GGATCCTTCC can be synthesized simply by joining the sequence TTCC to the 3'-end of the commercially available BamHI linker. The resulting sequence GGATCCTTCC has eight bases complementary to the 18S ribosomal RNA sequence, and should therefore provide an excellent initiation site for translation. Techniques similar to those previously disclosed may be employed to provide the requisite spacer nucleotides. In addition, the disclosed eucaryotic ribosomal binding site sequence can be joined to itself by blunt end ligation to provide two ribosomal binding sites, one adjacent to the initiation codon, the other ten base pairs away. Similarly, the procaryotic ribosomal binding site linker previously described can be employed as a spacer. The latter additionally provides a termination codon should it prove desirable to prevent read-through translation.

A more complete appreciation of the invention will be realized by reference to the following specific examples. Enterokinase and human proinsulin will be used in these examples for illustration purposes only. These examples are not intended to limit the invention disclosed herein except to the extent to which limitations appear in the appended claims. Reference to a prokaryotic host such as E. coli is made for convenience in the examples. The linkers of the present invention are also used for expression by a eukaryotic host following generally the principles of the invention and applying ordinary skill in the art.

EXAMPLE 1

This example describes the preparation of a cloned human proinsulin gene, synthesis of a specific cleavage linker and the joining of the two.

An isolated and purified (hereinafter "cloned") DNA sequence coding for human proinsulin is prepared as described in copending application Ser. No. 75,192.

Enterokinase is chosen as the specific cleavage means. The specific cleavage sequence for enterokinase is $NH_2$-Asp-Asp-Asp-Asp-Lys-COOH. The DNA squence of the plus strand coding for this amino acid sequence is 5'-GATGATGATGATAAA-3'. (The plus strand is defined as the strand whose nucleotide sequence corresponds to the mRNA sequence. The minus strand is the strand whose sequence is complementary to the mRNA sequence). This DNA sequence is the specific linker sequence and is chemically synthesized using the phosphotriester method described by Itakura, K., et al, supra.

The foregoing sequence is then blunt end ligated to the commercially available HindIII linker which, when cleaved with HindIII endonuclease yields a specific cleavage linker suitable for insertion at a HindIII site. The nucleotide sequence of both strands of the product linker is

AGCTTGGATGATGATGATAAA

ACCTACTACTACTATTT

By convention, the upper strand is the plus strand and is shown with the 5'-end to the left, the 3'-end to the right, the lower strand having the opposite polarity. Expression in either of the other two reading frames is provided by prior modification of the HindIII linker, either by the removal of one of the 3' terminal G's, or by addition of an extra 3' terminal G. The resulting sequence of the composite linker will be one nucleotide less or one nucleotide more, respectively, to provide for expression of the specific cleavage site sequence and the coding segment to which it is attached in correct reading frame.

The specific cleavage linker is blunt-end ligated with the cloned human proinsulin gene to produce a deoxynucleotide sequence of the plus strand containing: 5'-HindIII linker-specific cleavage linker-human proinsulin gene-3'.

EXAMPLE 2

This example describes the cloning of the deoxynucleotide sequence from Example 1 into a suitable expression plasmid and the expression of said coding sequence.

The specific cleavage linker-human proinsulin gene is inserted in an expression transfer vector. When insertion occurs in the correct orientation with respect to the initiation of translation at the insertion site, and the insert is in reading frame phase with the promoter and ribosome binding site, the protein product of the cloned coding segment is synthesized by actively metabolizing host cells transformed by the transfer vector.

When the cloned DNA coding segment codes for a peptide or small protein, it is preferable that the expression transfer vector contains a portion of a procaryotic gene between the promoter and the insertion site. The protein product in this instance is a fusion protein. The fusion protein tends to stabilize the foreign protein coded by the inserted gene in the intracellular milieu of the host. Excretion of the fusion protein from the host cell may also be accomplished by fusion with certain excretable host proteins, such as β-lactamase.

Expression plasmids have been developed wherein expression is controlled by the lac promoter (Itakura, K., et al, *Science* 198, 1056 (1977), Ullrich, A., et al, *Excerpta Medica,* (1979)); and by the β-lactamase promoter, (copending application of Baxter et al, Ser. No. 44,647, filed June 1, 1979, incorporated herein by reference).

The preferred method of constructing an expression plasmid is to chemically synthesize a DNA sequence containing a restriction site found within the β-lactamase gene and n deoxynucleotides where n=0, 1 or 2 in order to provide a proper reading frame. This sequence is then blunt-end ligated to the modified human proinsulin gene prepared in Example 1. This new DNA sequence and the transfer vector is then treated with the same restriction enzyme. See Heyneker, H. L. et al., supra, and Scheller, R. H. et al., supra. The new DNA sequence is then inserted into the transfer vector which is used to transform a host microorganism. A general inserted DNA sequence of the plus strand in accordance with the present invention can be shown as follows: 5'-restriction linker—$b_n c_m$—specific cleavage linker-cloned gene-3' where b an c may be any deoxynucleotide base and n and m are integers such that n+m=0, 1 or 2.

Expression is detected by measurement of a product capable of binding immunochemically with anti-insulin antibody or anti-proinsulin antibody. Fusion proteins indicative of expression are detected by comparing molecular weights of the host protein contributing the N-terminal part of the fusion protein in host cells transformed by expression plasmids with and without an insert.

The fusion protein for this specific example, having the formula X-Asp-Asp-Asp-Asp-Lys-Y, where X is a portion of the β-lactamase protein and Y is the human proinsulin protein, is purified using conventional techniques. The fusion protein is cleaved using enterokinase following the procedure as described by Liepnieks, supra. Gell electrophoresis is conducted to determine whether proper cleavage is obtained. Human proinsulin serves as the standard. Two bands are obtained from the cleavage product, one which migrates with the human proinsulin standard. Human proinsulin is then purified using conventional techniques.

EXAMPLE 3

A specific purification linker is provided by modifying the linker described in Example 1 having the sequence 5'-GATGATGATGATAAA-3'. The sequence is modified at the 3'-end by providing a C or preferably a T residue in place of the G. The modification can be accomplished by the use of T4 DNA polymerase in the presence of ATP and CTP to remove the 3'-terminal G, followed by S1 nuclease to remove the 5'-terminal C on the complementary strand. A C or preferably a T may be added to the 3'-end, either by enzymatic or chemical means. The resulting sequence codes for the amino acids AspAspAspAspAsn. The modified nucleotide sequence is then coupled by blunt end ligation to its unmodified homolog to yield 5'-GATGATGATGATAATGATGATGATGATAAA-3'.

The foregoing sequence is then connected to a HindIII linker as described in Example 1, and further connected with a coding segment as described in Example 1.

When expressed as a fusion protein, as described in Example 2, the linker will provide that the fusion protein contains a polyanionic portion of significant length. The fusion protein will therefore bind tightly to anion exchange materials such as diethylaminoethyl cellulose, even under conditions of ionic strength where substantially all other proteins in the cell lysate are eluted.

The fusion protein is then either eluted from the ion exchanger on treated in situ with enterokinase. In the latter case, preferential cleavage occurs at the junction bond and the desired protein is released from the ion exchanger. The procaryotic portion, bearing the polyanionic portion, remains bound to the ion exchanger. When the fusion protein is eluted from the ion exchanger prior to enterokinase treatment, incubation with enterokinase will cleave the junction bond preferentially and the procaryotic portion may be removed from the reaction mixture by preferential binding to an ion exchanger, as before. By the foregoing procedure, substantially quantitative purification of the desired protein is achieved in two steps.

EXAMPLE 4

In this example, the expression of a coding sequence such as that coding for human proinsulin is facilitated by the use of a ribosomal binding site linker. The nucleotide sequence AGGA is synthesized chemically by the method of Itakura, et al, supra. The synthetic sequence is then joined chemical or by blunt end ligation to the BamHI linker, GGATCC, obtained commercially from New England BioLabs, Cambridge, Mass. The resulting segment, AGGAGGATCC, is modified by treatment with BamHI endonunuclease followed by DNA polymerase I to fill in the single stranded protruding end to yield AGGAGGATC. Similarly, the coding segment is treated, first by the addition of a BamHI linker followed by modification of the linker with BamHI endonuclease and DNA polymerase I. The modified segments are then joined to each other by blunt end ligation to yield the sequence AGGAGGATCGATCC-coding segment. The start of the coding segment is then located six bases from the ribosomal binding site.

The sequence, ribosomal binding site-spacer-coding segment (human proinsulin) is further modified by the attachment of the appropriate restriction linker, depending on the desired insertion site. For example, EcoRI linker is used for insertion in the gene coding for β-galactosidase. In contrast to prior results, however, expression does not result in production of a fusion protein since the ribosomal binding site linker acts to reinitiate translation so that the segment coding for human proinsulin is expressed per se. The expression product is detected by immunochemical means.

EXAMPLE 5

The ribosomal binding site linker of Example 4, the specific purification segment of Example 3, and the specific cleavage linker of Example 1 are combined by blunt end ligation to yield a composite linker having the sequence AGGAGGATCGATCCATGGATGATGATGATAATGATGATGATGATAAA. Described in functional terms, the composite linker has the sequence ribosomal binding site-spacer-start codon-purification portion-specific cleavage site-coding segment. The composite is further modified by attachment of an EcoRI linker, to facilitate insertion into the $R_1$ site of a plasmid such as pBGP 120, described by Polisky, B., et al, supra. Transformation with the resulting transfer vector permits expression of human proinsulin having a polyanionic N-terminal portion. The expression product is then purified as described in Example 3 followed by specific cleavage using enterokinase. The combined techniques result in the production of highly purified human proinsulin. The principal advantage of the combined techniques is due to the fact that, once the appropriate linkers have been attached to the coding segment, expression of the coding segment and specific purification of the expression product are accomplished by relatively simple procedures which can be carried out without difficulty on a large scale.

As a further alternative, the above described composite linker can be further modified, prior to the addition of the restriction site linkers, by the addition of a sequence capable of functioning as a promoter, for example, TATGATG. The use of such a promoter sequence in combination with the linker segments just described makes it possible to obtain expression at a greater variety of insertion sites on the transfer vector, including those which are normally silent.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A recombinant DNA sequence which comprises three segments not contiguous in the natural environment, wherein a first segment encodes a eucaryotic protein and is contiguous with a second segment that encodes a specific cleavage sequence of at least two amino acids, said second segment being contiguous with a third segment, wherein:
   the expression product of said DNA is specifically cleaved by at least one enzymatic or chemical reagent at the peptide bond linking the eucaryotic protein and the specific cleavage sequence; and
   the third segment encodes a host peptide wherein the peptide is a polycationic peptide that is not natively associated with said eucaryotic protein.

2. A recombinant DNA sequence which comprises three segments not contiguous in the natural environment, wherein a first segment encodes a eucaryotic protein and is contiguous with a second segment that encodes a specific cleavage sequence of at least two amino acids, said second segment being contiguous with a third segment, wherein:
   the expression product of said DNA is specifically cleaved by at least one enzymatic or chemical reagent at the peptide bond linking the eucaryotic protein and the specific cleavage sequence; and
   the third segment encodes a host peptide wherein the peptide is a polyanionic peptide that is not natively associated with said eucaryotic protein.

3. A recombinant DNA sequence which comprises three segments not contiguous in the natural environment, wherein a first segment encodes a eucaryotic protein and is contiguous with a second segment that encodes a specific cleavage sequence of at least two amino acids, said second segment being contiguous with a third segment, wherein:
   the expression product of said DNA is specifically cleaved by at least one enzymatic or chemical reagent at the peptide bond linking the eucaryotic protein and the specific cleavage sequence wherein the enzymatic reagent is enterokinase, kallikrein B, or chymosin; and the third segment encodes a host peptide not natively associated with said eucaryotic protein.

4. A DNA cleavage sequence comprising the sequence CCAAGCTTGGAGGAGGATAATTCGATGGALGALGALGALAAKGALGALGALGALAAJ, wherein L is A, T, C or G, J is A or G, and K is T or C.

5. A recombinant DNA sequence which comprises three segments not contiguous in the natural environment, wherein a first segment encodes a eucaryotic protein and is contiguous with a second segment that encodes a specific cleavage sequence of at least two amino acids, said second segment being contiguous with a third segment, wherein:
   the expression product of said DNA is specifically cleaved by at least one enzymatic or chemical reagent at the peptide bond linking the eucaryotic protein and the specific cleavage sequence; and
   the third segment encodes a host peptide wherein the peptide is a hydrophobic peptide that is not natively associated with said eucaryotic protein.

6. An expression system capable of effecting the expression of the recombinant DNA sequence of any one of claims 1, 2, 3 or 5 in a suitable host cell.

7. A method for producing a recombinant protein in mature form which method comprises culturing the cells of claim 6, recovering the expression product, and cleaving the expression product with said specific reagent.

* * * * *